(12) United States Patent
Chanbasha et al.

(10) Patent No.: US 9,664,645 B2
(45) Date of Patent: May 30, 2017

(54) METHOD OF DETECTING AND QUANTIFYING PERCHLORATE CONTAMINATION

(71) Applicant: King Fahd University of Petroleum and Minerals, Dhahran (SA)

(72) Inventors: Basheer Chanbasha, Dhahran (SA); Hakimu Nsubuga, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 456 days.

(21) Appl. No.: 14/548,394

(22) Filed: Nov. 20, 2014

(65) Prior Publication Data

US 2016/0146753 A1  May 26, 2016

(51) Int. Cl.
| | |
|---|---|
| G01N 30/96 | (2006.01) |
| G01N 27/447 | (2006.01) |
| G01N 33/12 | (2006.01) |
| B01D 61/52 | (2006.01) |
| B01D 15/36 | (2006.01) |

(52) U.S. Cl.
CPC ........... *G01N 27/447* (2013.01); *B01D 15/36* (2013.01); *B01D 61/52* (2013.01); *G01N 33/12* (2013.01); *G01N 30/96* (2013.01)

(58) Field of Classification Search
CPC ...... G01N 27/447; G01N 33/12; G01N 30/96; G01N 2030/062; B01D 15/36; B01D 61/52; B01D 61/38; B01D 61/40
See application file for complete search history.

(56) References Cited

U.S. PATENT DOCUMENTS

2009/0294289 A1* 12/2009 Haslam .................. B01D 61/48
  204/524

FOREIGN PATENT DOCUMENTS

CN  103335990 A  10/2013
CN  103499475 A  1/2014

OTHER PUBLICATIONS

Dodds, et al. "Quantitative analysis of perchlorate in extracts of whole fish homogenates by ion chromatography: comparison of suppressed conductivity detection and electrospray ionization mass spectrometry" http://www.ncbi.nlm.nih.gov/pubmed/15221180, 2014, Abstract only.

Gu, et al. "Determination and Safety Evaluation of Heavy Metals in Canned Fish from Liaoning Coastal City" http://en.cnki.com.cn/Article_en/CJFDTOTAL-SPKJ201208008.htm, Feb. 2014. Abstract and citations only.

\* cited by examiner

*Primary Examiner* — Arun S Phasge
(74) *Attorney, Agent, or Firm* — Oblon, McClelland, Maier & Neustadt, L.L.P.

(57) ABSTRACT

A method of detecting and quantifying perchlorate contamination in samples, especially samples with complex background matrices such as food and produce with trace levels of perchlorate. A simple microwave assisted-electromembrane extraction provides simultaneous reduced extraction time, sample clean-up, high recovery and enrichment of perchlorate ions for detection and quantification by ion chromatography. Three parallel EME experiments connected to a single DC power supply improves the precision of the analyses. It also couples well with the multiple microwave digested samples and this reduces the sample preparation time and is hence suitable for routine environmental applications.

15 Claims, 5 Drawing Sheets

METHOD OF DETECTING AND QUANTIFYING PERCHLORATE CONTAMINATION

BACKGROUND OF THE INVENTION

Technical Field

The present invention relates to a method of measuring perchlorate contamination. More particularly, the present invention relates to a microwave assisted parallel electromembrane extraction method coupled with ion chromatography method to detect and quantify trace levels of perchlorate ions in produce, food and environments with complex background matrices.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Contamination by the ionic perchlorate ($ClO_4^-$) has increasingly become a human concern especially in areas surrounding aerospace operations, pyrotechnics and munitions (E. Urbansky, Environ. Sci. Pollut. R. 9 (2002) 187; E. T Urbansky, Biorem. J. 2 (1998) 81; Y. Liu, S. Mou, J. Chromatogr. A 997 (2003) 225; M. L. Magnuson, E. T. Urbansky, C. A. Kelty, Ana. Chem. 72 (2000) 25—each incorporated herein by reference in its entirety). Both aquatic and terrestrial species are prone to perchlorate contamination (P. N. Smith, C. W. Theodorakis, T. A. Anderson, R. J. Kendall, Ecotoxicology 10 (2001) 305; J. E. Canas, Q. Cheng, K. Tian, T. A. Anderson, J. Chromatogr. A 1103 (2006) 102—each incorporated herein by reference in its entirety). Such level of contamination is of profound toxicological interest since perchlorate can potentially interfere with normal thyroid function which leads to hormonal and metabolic disruptions (K. Saito, K. Yamamoto, T. Takai, S. Yoshida, Acta Endocrinologica 104 (1983) 456—each incorporated herein by reference in its entirety). The ion has a highly delocalized anionic charge and a large atomic volume resulting in low anionic charge density which facilitates the extreme solubility of the perchlorate salts in water matrices ((E. Urbansky, Environ. Sci. Pollut. R. 9 (2002) 187; P. N. Smith, Environ. Pollut. 132 (2004) 121; A. B. Kirk, E. E. Smith, K. Tian, T. A. Anderson, P. K. Dasgupta, Environ. Sci. Technol. 37 (2003) 4979—each incorporated herein by reference in its entirety). Evaluating tissue level contamination is paramount in determining significant toxicological and ecological exposure to perchlorate ion (A. B. Kirk, E. E. Smith, K. Tian, T. A. Anderson, P. K. Dasgupta, Environ. Sci. Technol. 37 (2003) 4979—incorporated herein by reference in its entirety). Up to date, suppressed ion chromatography (IC) coupled with conductivity detector has been used to quantify perchlorate to parts-per-billion (ppb) method detection limit (MDL) in water matrix without preconcentration (E. T. Urbansky, B. Gu, M. L. Magnuson, G. M. Brown, C. A. Kelty, J. Sci. Food Agric. 80 (2000) 1798; H. P. Wagner, B. V. Pepich, C. Pohl, D. Later, R. Joyce, K. Srinivasan, D. Thomas, A. Woodruff, B. Deborba, D. J. Munch, J. Chromatogr. A 1118 (2006) 85—each incorporated by reference in its entirety). However, with more complex background matrices, trace detection of perchlorate ion becomes very difficult (H. P. Wagner, B. V. Pepich, C. Pohl, D. Later, R. Joyce, K. Srinivasan, D. Thomas, A. Woodruff, B. Deborba, D. J. Munch, J. Chromatogr. A 1118 (2006) 85; T. W. Collette, T. L. Williams, E. T. Urbansky, M. L. Magnuson, G. N. Hebert, S. H. Strauss, Analyst 128 (2003) 88—each incorporated herein by reference in its entirety). Several clean-up methods that minimize ionic interferences have been suggested (A. B. Kirk, E. E. Smith, K. Tian, T. A. Anderson, P. K. Dasgupta, Environ. Sci. Technol. 37 (2003) 4979; T. A. Anderson, T. H. Wu, Bull. Environ. Contam. Toxicol. 68 (2002) 684; J. J. Ellington, J. J. Evans, J. Chromatogr. A 898 (2000) 193; P. B. Hatzinger, M. C. Whittier, M. D. Arkins, C. W. Bryan, W. J. Guarini, Remed. J. 12 (2002) 69; L. Guo, H. K. Lee, J. Chromatogr. A 1286 (2013) 9; M. Ericsson, A. Colmsjo, J. Chromatogr. A 964 (2002) 11—each incorporated herein by reference in its entirety). Typically, microwave-assisted extraction (MAE) in combination with solid phase extraction (SPE) for sample clean-up has widely been used in preparation of solid samples for instrumental analysis (C. Basheer, J. P. Obbard, H. K. Lee, J. Chromatogr. A 1068 (2005) 221—incorporated herein by reference in its entirety). As an alternative, electromembrane extraction (EME) has recently been used as a single step extraction method and its suitability, fits both charged and ionic compounds (K. F. Seipa, A. Gjelstad, S. Pedersen-Bjergaard, J. Chromatogr. A 1308 (2013) 37—incorporated herein by reference in its entirety). Its mode of operation appears in several scientific publications (C. Basheer, J. Lee, S. Pedersen-Bjergaard, K. E. Rasmussen, H. K. Lee, J. Chromatogr. A 1217 (2010) 6661; K. F. Seip, J. Stigsson, A. Gjelstad, M. Balchen, S. Pedersen-Bjergaard, J. Sep. Sci. 34 (2011) 3410; N. C. Dominguez, A. Gjelstad, A. M. Nadal, H. Jensen, N. J. Petersen, S. H. Hansen, K. E. Rasmussen, S. Pedersen-Bjergaard, J. Chromatogr. A 1248 (2012) 48—each incorporated by reference in its entirety). This method is capable of reducing the extraction time (K. F. Seipa, A. Gjelstada, S. Pedersen-Bjergaard, J. Chromatogr. A 1308 (2013) 37—incorporated herein by reference in its entirety). In most recent publications, EME has demonstrated good sample clean-up, good enrichment, less extraction time as well as low solvent consumption (K. F. Seip, J. Stigsson, A. Gjelstad, M. Balchen, S. Pedersen-Bjergaard, J. Sep. Sci. 34 (2011) 3410; N. C. Dominguez, A. Gjelstad, A. M. Nadal, H. Jensen, N. J. Petersen, S. H. Hansen, K. E. Rasmussen, S. Pedersen-Bjergaard, J. Chromatogr. A 1248 (2012) 48—each incorporated by reference in its entirety). Being a three-phase system, its analytes are preconcentrated in an aqueous acceptor phase giving the resultant extract an edge of direct compatibility with ion chromatography.

Accordingly, the objective of the present invention is to provide methods of quantifying perchlorate contamination in complex environmental matrices wherein detection limits are improved and co-elution of interfering ions present in sample extracts is minimized. A parallel EME mode used has advantages over single EME set-up since multiple samples are extracted simultaneously and this enhances the methods precision and shortens the time for parallel experiments (S. Jian-Nan, C. Juan, S. Yan-Ping, J. Chromatogr. A 1352 (2014) 1—incorporated by reference in its entirety).

BRIEF SUMMARY OF THE INVENTION

According to a first aspect, the present invention relates to method of detecting and quantifying perchlorate ions in a sample, comprising digesting the sample with an acid to form a sample solution, heating the sample solution in a solvent with a microwave digestion system to form a microwave-digested sample, extracting the perchlorate ions from the microwave-extracted sample with a parallel electromembrane extraction system by electromigration of the perchlorate ions across a membrane impregnated with a solvent and quantifying the perchlorate ions by ion chromatography. The electromembrane extraction system comprises three extraction setups connected parallel to a DC power supply and arranged in a single run.

In one embodiment, the heating is carried out for 10-15 min.

In one embodiment, the heating is carried out at a temperature of 60-150° C.

In one embodiment, the heating is carried out at 200-250 W.

In one embodiment, the heating is carried out at 20-50 V.

In one embodiment, the extracting is carried out for 10-15 min.

In one embodiment, the method has a limit of detection of lower than 0.05 µg per 1 g of the sample, based on a signal/noise ratio of 3.

In another embodiment, the method has a limit of detection of 0.04 µg 1 g of the sample, based on a signal/noise ratio of 3.

In one embodiment, the method has a limit of quantitation of lower than 0.15 µg per 1 g of the sample, based on a signal/noise ratio of 10.

In another embodiment, the method has a limit of quantitation of 0.125 µg per 1 g of the sample, based on a signal/noise ratio of 10.

In one embodiment, the solvent is selected from the group consisting of 1-hexanol, 1-octanol, 1-heptanol, 1-butyl-3-methylimidazolium tetrafluoroborate, 1-butyl-3-methylimidazolium octylsulfate and 1-butyl-3-methylimidazolium hexafluorophosphate.

In another embodiment, the solvent is 1-hexanol.

In one embodiment, the sample has a complex background matrix.

In one embodiment, the sample is selected from the group consisting of a pharmaceutical sample, a clinical sample, a chemical sample, an environmental sample, produce and food.

In one embodiment, the method provides mean perchlorate recovery of greater than 95%.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
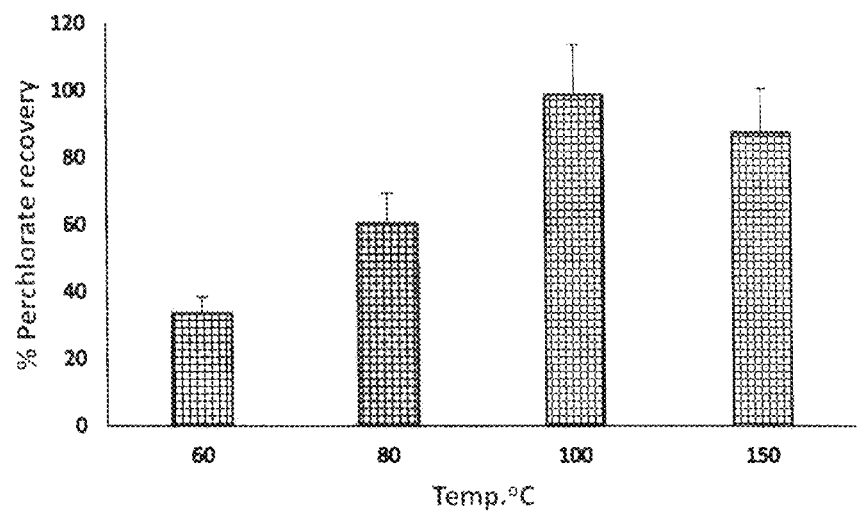
FIG. 1 is a bar graph illustrating the effect of MAD temperature on perchlorate extractability.

Referring now to the drawings, wherein like reference numerals designate identical or corresponding parts throughout the several views.

Perchlorate contamination is of profound toxicological interest, especially in areas of munitions, aerospace operations and pyrotechnics. Perchlorate is considered a marker of explosive chemicals and irrigation easily spreads the contamination to crops and livestock.

The present invention relates to a method of quantifying perchlorate contamination in a sample. This method is especially effective with samples with a complex background matrix such as food, produce and environmental samples wherein only trace amounts of perchlorate ions may be present. In this method, samples are digested in a microwave oven with an acid. Digested samples are then subject to a single step of electromembrane extraction for a simultaneous sample cleanup and enrichment or preconcentration of perchlorate ions. Three parallel experiments of EME are performed simultaneously by connecting to a single DC power supply, which improve the precision of the analyses. The perchlorate ions are then measured with an ion chromatography system.

For purposes of the present invention, trace levels or amounts of perchlorate ions generally refer to perchlorate ion concentrations of lower than 0.5 µg per 1 g of a sample, preferably lower than 0.1 gig, more preferably lower than 0.05 µg per 1 g of a sample.

For purposes of the present invention, a sample with a complex background matrix refers to any pharmaceutical, clinical, chemical and environmental sample, including produce (e.g. meat, seafood, vegetables, fruits) and food. The complex background matrices of these samples are attributed to the diversity of materials present, which typically include salts, acids, bases, metals, proteins and various organic and inorganic compounds with chemical properties similar to one another.

In one embodiment, a sample with a complex background matrix is specifically a seafood sample. For purposes of the present invention, seafood refers to fish and shellfish that are consumed as food by humans. Seafood differs from terrestrial animal meat especially in the high water and lipid content. The water content is normally greater than 75% in fish muscle while the lipid content is 5-25%. The types of lipids (e.g. fatty acids) in seafood and meat also differ. The protein content in fish muscle ranges from 15-21%. Water, being the main component of fish muscle, is divided into free water and water bound to proteins. Bound water is critical to the shelf life of seafood.

For purposes of the present invention, microwave-assisted digestion (MAD) is the process of heating solvents in contact with a sample with microwave energy to partition compounds of analytical interest from the sample matrix into a solvent such as water. The microwave radiation may be pulsed or continuous. In one embodiment, rotation may be begin upon radiation. In the case of the present invention, the compounds of analytical interest are perchlorate ions. MAD may further include an acid for the digestion of the sample. Examples of acids suitable for sample digestion include hydrochloric acid, nitric acid, sulfuric acid in concentrations of 25-250 mM, preferably 50-200 mM, more preferably 100-150 mM.

In one embodiment, MAD is carried out at a temperature of 50-175° C., preferably 60-150° C., more preferably 80-120° C., for example, 100° C.

In one embodiment, the MAD extraction/digestion time is 3-30 min, preferably 5-20 min, more preferably 10-15 min.

Microwave power is also crucial to the efficiency of MAD. In one embodiment, the microwave power is 50-500 W, preferably 100-300 W, more preferably 150-250 W, for example, 250 W.

For purposes of the present invention, electromembrane extraction (EME) is a sample preparation technique in pharmaceutical, chemical, clinical and environmental analysis. This technique uses electromigration across artificial liquid membranes or supported liquid membranes (SLMs) across a pH gradient from a donor solution to an acceptor solution for selective extraction of analytes and sample enrichment or preconcentration from complex matrices. The extraction and electromigration processes may be enhanced by constant stirring or agitation of the sample solution.

The SLMs are immobilized, thin-sheet membranes made of non-rigid materials such as polyethylene and polypropylene. These thin-sheet membranes are porous (0.1-0.3 μm) and are impregnated with a carrier solvent before they are dipped into a donor solution or an acceptor solution. The carrier solvent facilitates ion migration or ion exchange. Examples of solvents that are suitable as carrier solvents for SLMs include, but are not limited to, alcohols such as 1-hexanol, 1-octanol and 1-heptanol as well as ionic liquids such as 1-butyl-3-methylimidazolium tetrafluoroborate, 1-butyl-3-methylimidazolium octylsulfate and 1-butyl-3-methylimidazolium hexafluorophosphate. In one embodiment, the solvent is 1-hexanol.

EME may be carried at a wide range of pH values, for example pH 2-12. In one embodiment, the acceptor solution has a basic pH value, for example, pH 7.5 onwards, preferably pH 8-13, more preferably pH 11-12. In one embodiment, the donor solution has a pH value range of 4-8, preferably pH 5-7.5, more preferably a neutral pH range of 6-7.

Extraction times for the EME procedure are 3-30 min, preferably 5-20 min, more preferably 10-15 min.

The flux of perchlorate ions during EME may be carried out at a voltage of 5-250 V, preferably 10-100 V, more preferably 20-50 V. The preferred power range is 100-400 W, more preferably 150-300 W, even more preferably 200-250 W.

The limit of detection (LOD) for the perchlorate ion for the MAD-EME-IC method described herein, based on a signal/noise (S/N) ratio of 3, is lower than 0.1 μg per 1 g of a sample, preferably lower than 0.05 μg, more preferably lower than 0.04 μg. On the other hand, based on an S/N ratio of 10, the limit of quantitation (LOQ) for the perchlorate ion for the method is lower than 0.03 μg per 1 g of a sample, preferably lower than 0.02 μg, more preferably lower than 0.15 Low LOD and LOQ values are indicative of good performance. These relatively low LOD and LOQ values are attributed the target analyte in the complex matrix being subjected to a simultaneous selective EME extraction and sample clean-up.

Overall, the MAD-EME-IC method provides mean perchlorate recoveries of at least 85%, preferably greater than 95%, more preferably greater than 99%.

The examples below are intended to further illustrate protocols for the MAD-EME-IC extraction system with seafood samples, and are not intended to limit the scope of the claims.

EXAMPLE 1

Chemicals and Materials

All chemicals used were of reagent grade and deionized water of greater than 18 M Ω-cm resistivity generated through a Milli-Q purification system (Millipore, Mass., and USA) was used throughout the experiment. Sodium hydroxide, potassium hydroxide, sodium chloride, nitric acid were obtained from J. T. Baker (Philips Burg, N.J.). HPLC-grade organic solvents and room temperature ionic liquids (1-butyl-3-methylimidazolium tetrafluoroborate (C4MIM[BF4]), 1-butyl-3-methylimidazolium octylsulfate (C4MIM[OcSO4]), and 1-butyl-3-methylimidazolium hexafluorophosphate (C4MIM[PF6]) for EME extractions were secured from Sigma Aldrich (Milwaukee, Wis., USA) and Strem Chemicals (Newburyport, Mass., USA) respectively. An ES 0300 with programmable voltage (0-300V) and with a current output in the range from 0 to 450 mA (Delta Elektronika BV, Zierikzee, The Netherlands) was used for power supply. The electrodes used were platinum wires of diameter 0.5 mm (K. A. Rasmussen, Hamar, Norway). Polypropylene membrane Sheet (157 μm thickness, 0.2 μm pore size) (Membrana, Wuppertal, Germany) was used in the fabrication of EME membrane envelopes.

Agitation, during extraction was performed on a vibramax 100 agitator (Heidolph, Kelheim, Germany). Standard stock solution of sodium perchlorate at 100 μg/mL was prepared in deionized water and refrigerated at 4° C. From the 100 μg/mL stock solutions, working standards were prepared in 100 mL volumetric flasks.

EXAMPLE 2

Microwave Assisted Digestion (MAD) System

Multiwave 3000 (Anton Paar, Graz, Austria) with software version v1.52 was used for closed-vessel extractions. The system consisted of 16 high pressure polytetrafluoroethylene (PTFE) vessels of capacity 100 mL (240° C., temperature and 40 bars, pressure). Before and after use, all plastic and glass ware were washed with concentrated nitric acid and copious amounts of milli-Q water.

The efficiency of the MAD process is directly related to the operation conditions selected (A. Gjelstad, K. E. Rasmussen, S. Pedersen-Bjergaard, J. Chromatogr. A 1174 (2007) 104—incorporated herein by reference in its entirety). These operation condition factors include temperature, time and power of the MAD process. The operating conditions (power, 250 W; 10 min ramp to 100° C.; and 25 mL solvent volume) were used in the preliminary experiments for selecting the best extraction conditions. Water was selected as an extracting solvent basing on its excellent solubility and better microwave absorbing properties (L. Xu, H. K. Lee, J. Chromatogr. A 1192 (2008) 203; C. Basheer, J. P. Obbard, H. K. Lee, J. Chromatogr. A 1068 (2005) 221—each incorporated herein by reference in its entirety).

Microwave heating is a product of ionic conduction and dipole rotation generated from the effect of microwaves on molecules (A. Gjelstad, K. E. Rasmussen, S. Pedersen-Bjergaard, J. Chromatogr. A 1174 (2007) 104—incorporated herein by reference in its entirety). 25 ml of 100 mM $HNO_3$ facilitates the digestion process of the seafood samples. The electrophoretic migration of ions in the digestion solvent creates friction and heats up the solvent (A. Gjelstad, K. E.

Rasmussen, S. Pedersen-Bjergaard, J. Chromatogr. A 1174 (2007) 104—incorporated herein by reference in its entirety).

The heat generated contributes to increased analyte recoveries. Because closed vessels are used, the temperatures may exceed the boiling points of the extracting solvents. The rising temperatures results in to elevated extraction efficiencies. As a result, the experiment was conducted at temperatures of 60, 80, 100° C. FIG. 1 shows the MAD temperature profile. High temperatures result to higher extraction efficiency as reflected in the extraction yield.

At elevated temperatures, matrix effects from co-eluting residual matrix components result into a condition that compromises the perchlorate peak. At this temperature, solvents have higher capacity to solubilize analytes.

In MAD, the period of heating is of great significance and the extraction times are usually very short compared to conventional techniques. This is aimed at avoiding possible thermal degradation and oxidation typical of target compounds sensitive to overheating (A. Slampova, P. Kuban, P. Bocek, J. Chromatogr. A 1234 (2012) 32—incorporated herein by reference in its entirety).

For this reason, the effect of micro wave extraction time in a range of 5 to 20 min was evaluated. Above 10 min, there did not appear to be any significant increase in extraction registered. Irradiation time is also influenced by the dielectric properties of the solvent. Because water was used as an extracting solvent, it might have heated up tremendously on longer exposure time affecting our target analytes.

Microwave power is directly related to the quantity of sample and the extraction time required. For a closed vessel system, power selection depends on the number of samples to be extracted during one extraction run. 16 vessels were treated in one run. Careful power selection reduces excessive temperatures that would otherwise result to analyte degradation and excessive pressure inside the vessels. As a result, the experiment was evaluated on power ratings of 100, 150, 250 and 300 W (see FIG. 3).

Microwave power and temperature are interrelated. Hence, increasing microwave power increases the overall temperature of the system and this result to a decrease in extraction yield not until it becomes insignificant or declines (C. S. Eskilsson, E. Bjorklund, J. Chromatogr. A, 902 (2000) 227—incorporated herein by reference in its entirety).

EXAMPLE 3

Electromembrane Extraction (EME) Procedure

To avoid ionic interference and co-elution during perchlorate analysis with IC, the MAD extracts are further preconcentrated using EME technique. Three parallel experiments of EME are performed simultaneously by connecting to a single DC supply as this couples well with the multiple samples obtained from microwave digestion. Factors in EME such as SLM, pH for both donor and acceptor solutions, extraction time and applied voltage were all investigated.

Membrane bags were prepared by cutting commercial polypropylene flat-sheet membranes into rectangular sheets (H. Nsubuga, C. Basheer, J. Chromatogr. A 1315 (2013) 47—incorporated herein by reference in its entirety) with dimensions of 1.0 cm by 1.5 cm. The shorter (1.0 cm) edge was folded over to a width of 0.8 cm and later heat-sealed with an electrical sealer. One of the two remaining open ends was similarly heat-sealed to create an envelope. More than ten envelopes could conveniently be fabricated within one hour.

The membrane envelopes were first impregnated for 10 sec with 1-hexanol and then filled with 150 µL of 100 mM NaOH (acceptor solution) using a 250 µL Hamilton syringe. For IL-EME experiment, the membrane envelope was immersed into a mixture of IL and methanol in a ratio of 2:1 for 10 s before filling with NaOH. Two platinum electrodes were used as anode and cathode by dipping into the membrane envelope containing the acceptor solution and the entire digested sample solution (donor phase) respectively.

The membrane envelope holding an acceptor phase formed a 3-phase system when immersed into the donor solution contained in an extraction vial. Three sets of extraction setup connected to one DC power supply in parallel could be arranged in a single run. A magnetic stir bar, placed into the extraction glass vial, ensured constant stirring of the entire sample solution (25 mL). Varying voltage was continuously monitored using a voltmeter. The electrodes were later connected to the power supply and the experiment ran at a fixed potential for a certain period of time. MAD-EME experiment was performed for 10 min at a voltage of 12 V and at a stirring rate of 160 rpm. At this potential, the $ClO_4^-$ ions migrated from the donor compartment across the SLM to the acceptor phase. After the extraction, the voltage was switched off and 120 µL of the acceptor solution was withdrawn with a microsyringe and later injected in to an IC system for analysis.

A magnetic stir bar, placed into the glass vial, ensured constant stirring of the entire sample solution (25 mL). Varying voltage was continuously monitored using a voltmeter.

The suitability of a solvent as SLM plays a key role in EME experiments (C. H. Chan, R. Yusoff, G. C. Ngoh, F. W. Kung, J. Chromatogr. A 1218 (2011) 6213; T. Y. Tan, C. Basheer, K. P. Ng, H. K. Lee, Anal. Chim. Acta 739 (2012) 31—each incorporated herein by reference in its entirety). The solvent facilitates the electrokinetic cross-membrane extraction. The flux of analyte during extraction is determined by the gradient of analyte concentration across the SLM which once fine-tuned contributes to analyte selectivity as well as good sample clean-up (T. Y. Tan, C. Basheer, K. P. Ng, H. K. Lee, Anal. Chim. Acta 739 (2012) 31; T. M. Middelthon-Bruer, A. Gjelstad, K. E. Rasmussen, S. Pedersen-Bjergaard, J. Sep. Sci. 31 (2008) 753—each incorporated herein by reference in its entirety).

Figure 2:
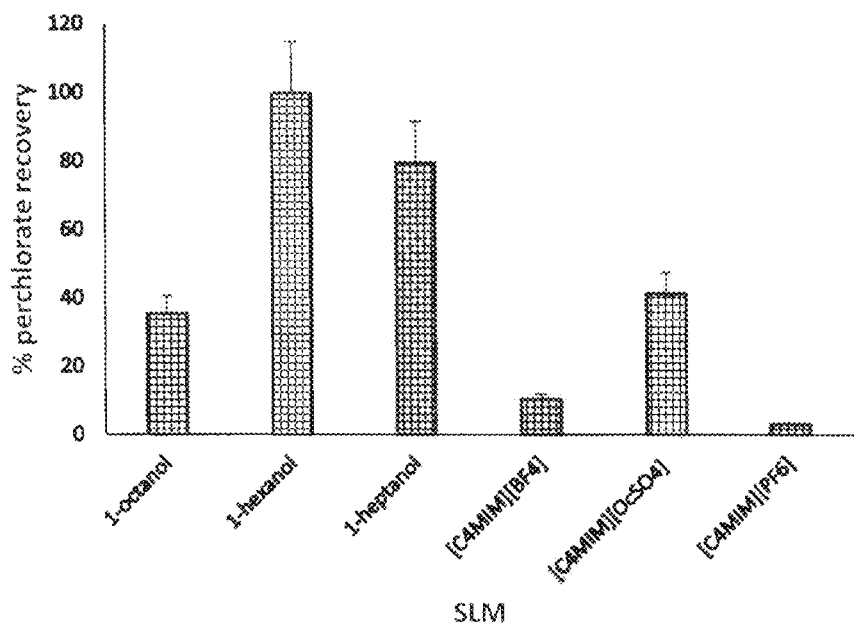
FIG. 2 is a bar graph illustrating the influence of SLM on extraction performance of MAD-EME extraction.

The main factors considered for SLM suitability are, current stability during EME process and selectivity for the perchlorate ion. Hence, alcohols (1-hexanol, 1-octanol, and 1-heptanol) plus ionic liquids, as shown in FIG. 2, were evaluated to determine their extraction efficacy for perchlorate anion. Ionic liquids (ILs) used are represented as (C4MIM[BF4]), (C4MIM[OcSO4]) and (C4MIM[PF6]) respectively.

Results showed that 1-hexanol gave higher extraction efficiency and selectivity for $ClO_4^-$ ion. The reason for the superior extraction efficacy of 1-hexanol is not clear at the moment. However, 1-octanol and ionic liquids when used as SLM gave excessive and unstable current drops.

The charged forms of the analyte are cardinal in achieving maximum EME efficiency. This is because the electrical potential difference serves as the methods driving force generator.

From the above premise, pH adjustments of both the acceptor and donor solutions facilitated mass movements of $ClO_4^-$ ions along the pH gradient. Using 100 mM NaOH and 100 mM $HNO_3$, the pH of both solutions were adjusted accordingly.

In both phases, investigations were conducted at pH 2, 4, 8 and 12. Nitric acid was chosen for pH modulation since the nitrate peak does not co-elute with that of the perchlorate.

Figure 4A:
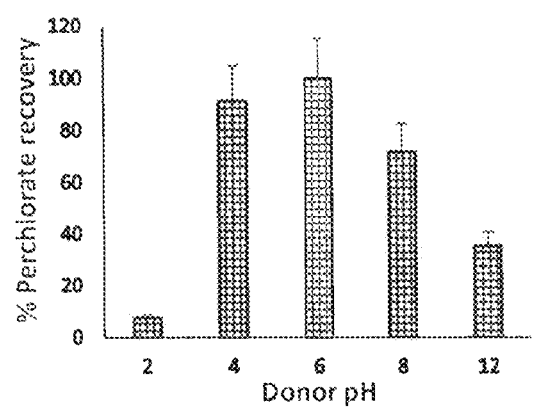
FIG. 4a is a bar graph illustrating the effect of pH adjustments of the donor solution on perchlorate extractability.
Figure 4B:
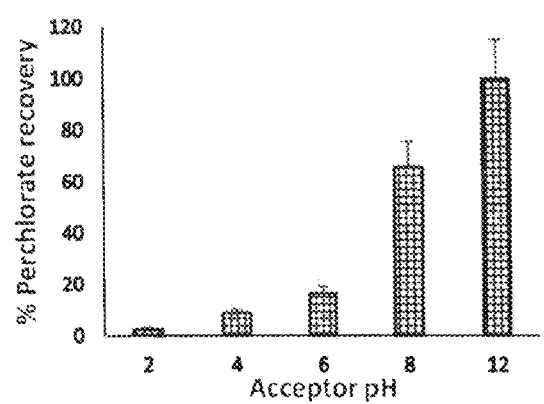
FIG. 4b is a bar graph illustrating the effect of pH adjustments of the acceptor solution on perchlorate extractability.

FIG. 4 illustrates the pH profiles for both the donor and the acceptor solutions.

Perchlorate extraction was favored by the basic pH of the acceptor phase. Poor perchlorate ion extraction was eminent at lower pH values. However at pH 6, there was higher extraction efficacy as this appeared to be a more favorable pH for the donor solution. Because the pH of milli-Q water used was 5.8 which is a value close to 6, all the proceeding experiments were performed without donor pH adjustments. At such pH, the perchlorate ion will be in its ionized form thus facilitating electrical conductivity. Such trend is theoretically well supported (A. Gjelstad, K. E. Rasmussen, S. Pedersen-Bjergaard, J. Chromatogr. A 1124 (2006) 29—incorporated herein by reference in its entirety).

EME is an equilibrium-based extraction and as such was demonstrated to offer fast extractions in relation to liquid-liquid extractions which are exhaustive (A. Gjelstad, K. E. Rasmussen, S. Pedersen-Bjergaard, J. Chromatogr. A 1174 (2007) 104—incorporated herein by reference in its entirety). To determine the most favorable extraction time, the experiment was conducted at extraction times of 5, 10, 15 and 25 minutes.

Figure 5:
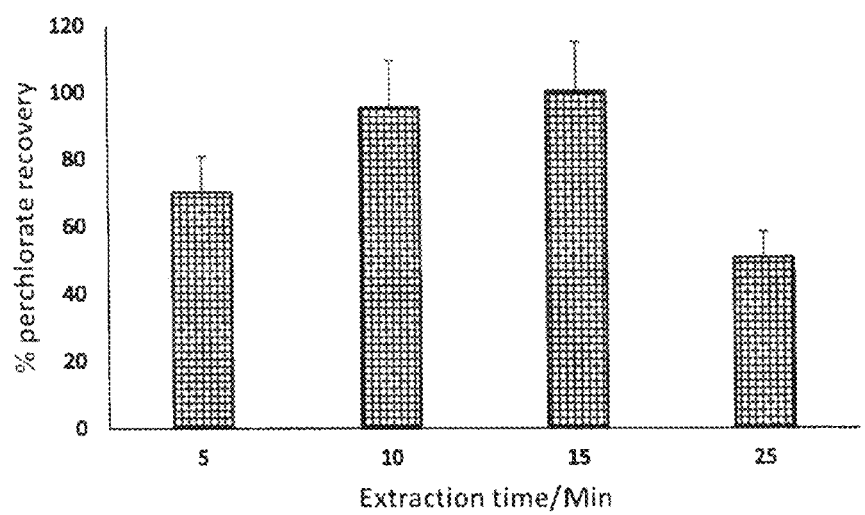
FIG. 5 is a bar graph illustrating the EME extraction time profile.

Results in FIG. 5 indicate that the EME system attained maximum extraction in 10 min and 15 min. At this time, the system might have entered a steady state condition resulting in to minimal gain in transfer. A similar trend has been observed in the previous reports (A. Gjelstad, K. E. Rasmussen, S. Pedersen-Bjergaard, J. Chromatogr. A 1124 (2006) 29—incorporated herein by reference in its entirety). After 15 minutes, the system registers a decrease in extraction efficiency which is attributed to depletion of SLM solvent over time. This results into back migration of the analytes and hence, lower preconcentration. Still, the current becomes erratic possibly due to depletion of the organic solvent serving as SLM and this compromises the integrity of the membrane. As a result, 10 min extraction time was adopted for further experiments.

Figure 3:
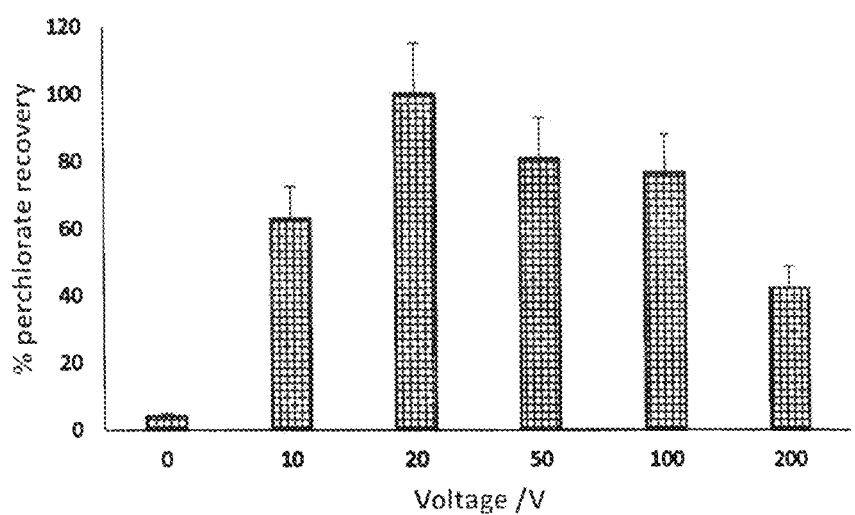
FIG. 3 is a bar graph illustrating the selection of suitable voltages for the MAD-EME experiment.

The flux of analytes during extraction varies with the applied voltage and in one of the EME mathematical model; it is postulated that, increasing voltage enhances extractability of target analytes (S. Pedersen-Bjergaard, K. E. Rasmussen, J. Chromatogr. A, 1109 (2006) 183; A. Gjelstad, K. E. Rasmussen, S. Pedersen-Bjergaard, J. Chromatogr. A 1124 (2006) 29 each incorporated herein by reference in its entirety). However, when sufficient extraction time is provided, equivalent recoveries can be obtained (I. K. Kiplagat, T. K. Doan, P. Kuban, P. Bocek, Electrophoresis 32 (2011) 3008; A. Gjelstad, T. M. Andersen, K. E. Rasmussen, S. Pedersen-Bjergaard, J. Chromatogr. A 1157 (2007) 38—each incorporated herein by reference in its entirety). The EME system was evaluated at vary varying potentials ranging from 0 to 200 V for 10 minutes as shown in FIG. 3. There was almost zero transfer of perchlorate ions in to the acceptor solution observed at zero potential. The probable reason seemed to be that diffusion was not yet forthcoming in such a shortest time. However, as voltage was applied to the EME system, the negatively charged perchlorate ions migrated to the direction of the anode across the SLM. Constant stirring of the donor solution ensured efficient replenishment and transfer of the ions in to the acceptor phase. Voltages higher than 20V generated current flow fluctuations. As a result, excessive bubble formation was witnessed at the electrodes, though this was not investigated. These results show that a lower voltage can provide higher extraction efficiency. Precisely, the explanation for this observation is that the entire EME setup is an electric circuit, in which the SLM acts as an electric resistance, and the charged analytes follow the path of the electric current. The current must therefore be kept small to prevent electrolysis that would otherwise affect the mass transfer and reduce the $ClO_4^-$ extraction efficiency. 20V was then selected for subsequent experiments.

EXAMPLE 4

Ion Chromatography (IC) System

Analysis was carried out using Dionex (Sunnyvale, Calif., USA) ICS-2000 IC system equipped with a gradient pump, an eluent generator, an auto sampler, an LC 30 chromatography oven, a conductivity detector, a 2 mm anion self-regenerating suppressor, suppressor external regen installation kit for external water mode and conductivity meter (Thermo orion). Dionex ion pac (AG16) guard analytical column was used for ion separation. System control was monitored using chromeleon 6.5 chromatography workstation software. The system conditions were set as: eluent=50 mM sodium hydroxide; flow rate=1.0 mL/min; injection volume=100 µL and temperature=30° C. Suppressed conductivity in the external water mode was used for ion detection.

EXAMPLE 5

MAD-EME Sample Preparation

Fresh seafood samples were purchased from local fish markets of Al-khobar in the eastern province of Saudi Arabia. The study attempted to include trivally fish, striped red mullet, barracuda fish, emperor fish, Indian mackerel, solea (flat fish), oysters, crab, squid, and shrimp as representative seafood species within the community. A minimum of two specimens from each individual species were randomly selected, transported to the laboratory in an icebox for temporary storage and at 4° C. The frozen samples were then thawed and allowed to reach room temperature, gutted, fileted and minced prior to microwave digestion.

In an exemplary MAD-EME experiment with a spiked oyster sample, a 3 g of oyster sample and 25 mL of 100 mM HNO$_3$ solution was introduced into each sealed PTFE microwave vessel. Digestion was performed at a temperature of 100° C. and irradiation power of 250 W. Desired temperatures were achieved by varying the digestion time from 5 min followed by a holding time of 10 min. After cooling, the vessels were opened and the solution transferred into an EME set up as a donor solution for simultaneous extraction and clean-up procedure.

The acceptor solution constituted 150 μL of 100 mM NaOH. One platinum electrode was inserted in to the acceptor solution, while the second one into the donor solution. The electrodes were later connected to the power supply and voltage turned on. The extraction was performed for 10 min and at a stirring speed of 700 rpm. At this potential, the ClO$_4^-$ ions migrated from the donor compartment across the SLM to the acceptor phase. After the extraction, the voltage was switched off and 120 μL of the acceptor solution was injected in to IC system for analysis.

EXAMPLE 6

Assessment of the MAD-EME-IC Method

The objective of the present invention is to develop an analytical method for trace determination of perchlorate ions in biological samples. The method is to reduce the level of matrix interferences without compromising the perchlorate peak and would also offer high extraction efficiency at reduced cost and in a comparably shorter time.

To assess the suitability and practicability of the developed MAD-EME-IC method, parameters such as linearity, repeatability, limits of detection and quantification were investigated.

Perchlorate peak areas were plotted against spiked concentrations in seafood sample solutions to generate corresponding calibration curves. The linearity of this method was evaluated at five spiking concentration levels ranging from 1 to 125 μg/g. Analytical parameters of the developed MAD-EME-IC method for perchlorate ion determination were compared to the same method at zero potential. Good linearity with coefficient of determination ($r^2$) of ≥0.9949 was observed. Satisfactory reproducibility of relative standard deviations (RSD) 4.3% (n=4) was obtained.

The limit of detection (LOD) for the perchlorate ion was determined based on a signal/noise (S/N) ratio of 3 and was found to be 0.04 μg/g while LOQ value of 0.125 μg/g was obtained on a signal/noise (S/N) ratio of 10. By comparing the perchlorate peak areas at different extraction conditions, corresponding enrichment factors were obtained. These values are summarized in Table 1.

To evaluate the accuracy of the proposed method, the extraction recoveries were performed on nine seafood samples spiked with perchlorate standard each at three different concentrations as outlined in Table 3.

The MAD-EME-IC method developed according to the present invention was applied to ten different types of seafood samples collected from local markets of Al-khobar, Saudi Arabia to examine its applicability. The results obtained are as shown in Table 2. No perchlorate anion was detected in crab samples by this method and the concentration obtained for the rest of the seafood samples were near the LOD. To evaluate the matrices' interference of the MAD-EME-IC developed method, one sample was spiked with varying concentrations (n=4), and extraction recoveries calculated based on standard addition recoveries.

TABLE 2

Concentration of perchlorate in different seafood samples collected from local markets in Al-khobar.

| English name | Concentration of ClO$_4^-$ (μg/g) |
|---|---|
| Trivally fish | 0.92 ± 0.40[a] |
| Stripped red mullet | 0.83 ± 0.17 |
| Barracuda fish | 0.45 ± 0.61 |
| Emperor fish | 0.54 ± 0.43 |
| Indian Mackerel | 0.73 ± 2.70 |
| Solea | 0.68 ± 0.93 |
| Oyster | 0.69 ± 0.02 |
| Crab | nd |
| Squid | 0.51 ± 0.62 |
| Shrimp | 0.86 ± 2.30 | nd: not detected
[a] mean standard deviation of 3 different analyses from 3 different concentrations of perchlorate.

Results in Table 3 indicate that the mean recoveries in all the samples tested ranged between 85.2 to 107%. The relatively high mean recoveries indicate low matrix effect interferences. From the results, it is feasible for the developed method to detect and quantify perchlorate ions in seafood samples.

TABLE 3

Mean recovery studies performed on one of the seafood samples.

| English name | Added amount (μg/g) | Mean Recovery % (n = 4) | RSD[a] % (n = 6) |
|---|---|---|---|
| Trivally fish | 125 | 107.0 | 3.8 |
|  | 100 | 90.5 | 4.8 |
|  | 50 | 85.2 | 6.8 |

TABLE 1

Analytical parameters of the developed MAD-EME-IC method for determination of perchlorate compared to MAD-EME-IC method at zero potential.

| | Linear | | | | MAD-EME-IC[d] | | MAD-LPME-IC[e] | |
|---|---|---|---|---|---|---|---|---|
| Analyte | range (μg/g) | $r^{2a}$ | LOD[b] μg/g | LOQ[c] μg/g | Enrichment factor | RSD[f] %, n = 4 | Enrichment factor | RSD %, n = 4 |
| ClO$_4^-$ | 1-125 | 0.9949 | 0.04 | 0.1245 | 15.6 | 4.3 | 1.4 | 7.8 |

[a] coefficient of determination,
[b] limit of detection,
[c] limit of quantitation
[d] MAD-EME-IC,
[e] MAD-LPME-IC (zero potential),
[f] Relative standard deviation TABLE 3-continued Mean recovery studies performed on one of the seafood samples.

| English name | Added amount (μg/g) | Mean Recovery % (n = 4) | RSD[a] % (n = 6) |
|---|---|---|---|
| Stripped red mullet | 125 | 99.3 | 3.4 |
|  | 100 | 98.2 | 1.2 |
|  | 50 | 90.0 | 2.6 |
| Barracuda fish | 125 | 103.0 | 1.1 |
|  | 100 | 96.7 | 6.7 |
|  | 50 | 96.2 | 3.5 |
| Emperor Fish | 125 | 106.3 | 2.1 |
|  | 100 | 101.2 | 0.9 |
|  | 50 | 94.9 | 0.7 |
| Indian Mackerel | 125 | 100.5 | 1.7 |
|  | 100 | 99.0 | 1.4 |
|  | 50 | 90.0 | 2.1 |
| Solea | 125 | 105.4 | 3.3 |
|  | 100 | 97.0 | 2.6 |
|  | 50 | 90.0 | 1.8 |
| Crab | 125 | 100.9 | 3.6 |
|  | 100 | 99.8 | 4.3 |
|  | 50 | 96.0 | 2.2 |
| Squid | 125 | 104.6 | 1.6 |
|  | 100 | 94.5 | 1.9 |
|  | 50 | 93.8 | 3.5 |
| Shrimp | 125 | 100.5 | 0.8 |
|  | 100 | 102.2 | 1.6 |
|  | 50 | 98.0 | 1.8 |

[a]relative standard deviation

Therefore, trace determination of perchlorates in seafood samples was feasible by a combination of MAD, EME, and IC-Conductivity detector. The developed MAD-EME-IC method demonstrated to be an effective tool for trace level determination of perchlorate in seafood samples. The method was compared to passive diffusion in which no voltage was applied and it proved to be more efficient, providing relatively higher enrichment in a less time. Moreover, each EME disposable membrane bag was used for one analysis and this eliminated associated carry over effects.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method of detecting and quantifying perchlorate ions in a sample, comprising:
digesting the sample with an acid to form a sample solution;
heating the sample solution in a solvent with a microwave digestion system to form a microwave-digested sample;
extracting the perchlorate ions from the microwave-extracted sample with a parallel electromembrane extraction system by electromigration of the perchlorate ions across a membrane impregnated with a solvent; and
quantifying the perchlorate ions by ion chromatography;
wherein the electromembrane extraction system comprises three extraction setups connected parallel to a DC power supply and arranged in a single run.

2. The method of claim 1, wherein the heating is carried out for 10-15 min.

3. The method of claim 1, wherein the heating is carried out at a temperature of 60-150° C.

4. The method of claim 1, wherein the heating is carried out at 200-250 W.

5. The method of claim 1, wherein the heating is carried out at 20-50 V.

6. The method of claim 1, wherein the extracting is carried out for 10-15 min.

7. The method of claim 1, wherein the method has a limit of detection of lower than 0.05 μg per 1 g of the sample, based on a signal/noise ratio of 3.

8. The method of claim 1, wherein the method has a limit of detection of 0.04 μg per 1 g of the sample, based on a signal/noise ratio of 3.

9. The method of claim 1, wherein the method has a limit of quantitation of lower than 0.15 μg per 1 g of the sample, based on a signal/noise ratio of 10.

10. The method of claim 1, wherein the method has a limit of quantitation of 0.125 μg per 1 g of the sample, based on a signal/noise ratio of 10.

11. The method of claim 1, wherein the solvent is selected from the group consisting of 1-hexanol, 1-octanol, 1-heptanol, 1-butyl-3-methylimidazolium tetrafluoroborate, 1-butyl-3-methylimidazolium octylsulfate and 1-butyl-3-methylimidazolium hexafluorophosphate.

12. The method of claim 1, wherein the solvent is 1-hexanol.

13. The method of claim 1, wherein the sample has a complex background matrix.

14. The method of claim 1, wherein the sample is selected from the group consisting of a pharmaceutical sample, a clinical sample, a chemical sample, an environmental sample, produce and food.

15. The method of claim 1, wherein the method provides mean perchlorate recovery of greater than 95%.

* * * * *